(12) United States Patent
Fisher et al.

(10) Patent No.: US 7,442,196 B2
(45) Date of Patent: Oct. 28, 2008

(54) DYNAMIC KNEE BALANCER

(75) Inventors: Michael G. Fisher, Folsom, CA (US);
Anthony K. Hedley, Paradise Valley, AZ (US); Michael Howard, Scottsdale, AZ (US); Kevin Cordes, Placerville, CA (US); Toshinobu Katsuya, Kobe (JP)

(73) Assignee: Synvasive Technology, Inc., El Dorado Hills, CA (US)

( * ) Notice: Subject to any disclaimer, the term of this patent is extended or adjusted under 35 U.S.C. 154(b) by 287 days.

(21) Appl. No.: 10/773,608

(22) Filed: Feb. 6, 2004

(65) Prior Publication Data
US 2005/0177169 A1    Aug. 11, 2005

(51) Int. Cl.
*A61B 17/17* (2006.01)
*A61B 17/58* (2006.01)
*A61B 17/90* (2006.01)

(52) U.S. Cl. .............. 606/88; 606/120; 606/96

(58) Field of Classification Search ............. 606/86–88; 623/20.14–20.36
See application file for complete search history.

(56) References Cited

U.S. PATENT DOCUMENTS

| | | | |
|---|---|---|---|
| 4,220,146 A | 9/1980 | Cloutier | |
| 4,501,266 A | 2/1985 | McDaniel | |
| 4,524,766 A | 6/1985 | Petersen | |
| 4,567,886 A | 2/1986 | Petersen | |
| 5,197,488 A * | 3/1993 | Kovacevic | 600/595 |
| 5,207,711 A | 5/1993 | Caspari et al. | |
| 5,344,461 A * | 9/1994 | Phlipot | 623/20.16 |
| 5,464,406 A | 11/1995 | Ritter et al. | |
| 5,470,354 A | 11/1995 | Hershberger | |
| 5,514,183 A * | 5/1996 | Epstein et al. | 623/20.23 |
| 5,520,695 A * | 5/1996 | Luckman | 606/88 |
| 5,540,696 A | 7/1996 | Booth, Jr. et al. | |
| 5,597,379 A | 1/1997 | Haines et al. | |

(Continued)

FOREIGN PATENT DOCUMENTS

EP    1 402 857    3/2004

OTHER PUBLICATIONS

Delio, "Hoping for a Knee-Jerk Reaction" Wired News. 2004.,[retrieved on Aug. 22, 2005]. Retrieved from the Internet on <URL: http://wiredvig.wired.com/news/medtech/0,1286,62716,00. html?tw=newsletter_to>.

(Continued)

*Primary Examiner*—Eduardo C. Robert
*Assistant Examiner*—Mary Hoffman
(74) *Attorney, Agent, or Firm*—Townsend & Townsend & Crew LLP

(57) ABSTRACT

Dynamic knee balancing devices, systems and methods provide for enhanced total knee arthroplasty ("TKA") procedures. Devices generally include a stationary femoral member for removably attaching to a distal femur and an adjustable femoral member coupled with the stationary member for adjusting ligament tension of the knee. The adjustable femoral member includes at least one positioning feature for providing positional and/or orientation information for facilitating the TKA procedure. Additionally, the adjustable femoral member is movably couplable with a tibial member engaged with the proximal tibia to allow movement of the knee through a range of motion without removing the device from the joint space. When the adjustable femoral member is adjusted, the positional feature(s) move relative to the distal femur to provide positional information.

40 Claims, 11 Drawing Sheets

U.S. PATENT DOCUMENTS

| | | | |
|---|---|---|---|
| 5,630,820 A | | 5/1997 | Todd |
| 5,649,929 A | | 7/1997 | Callaway |
| 5,656,785 A | | 8/1997 | Trainor |
| 5,688,282 A | * | 11/1997 | Baron et al. ............... 606/90 |
| 5,733,292 A | * | 3/1998 | Gustilo et al. ............... 606/88 |
| 5,735,904 A | | 4/1998 | Pappas |
| 5,755,801 A | * | 5/1998 | Walker et al. ........... 623/20.21 |
| 5,782,925 A | * | 7/1998 | Collazo et al. ........... 623/20.28 |
| 5,800,438 A | | 9/1998 | Tuke et al. |
| 5,860,980 A | * | 1/1999 | Axelson et al. ............... 606/88 |
| 5,879,394 A | * | 3/1999 | Ashby et al. ............ 623/20.33 |
| 5,880,976 A | | 3/1999 | DiGioia, III |
| 5,911,723 A | | 6/1999 | Ashby et al. |
| 6,022,377 A | | 2/2000 | Nuelle et al. |
| 6,056,756 A | | 5/2000 | Eng et al. |
| 6,068,658 A | * | 5/2000 | Insall et al. ............... 623/20.3 |
| 6,096,043 A | | 8/2000 | Techiera et al. |
| 6,296,666 B1 | * | 10/2001 | Gardner ................ 623/20.29 |
| 6,361,564 B1 | * | 3/2002 | Marceaux et al. ........ 623/20.29 |
| 6,488,711 B1 | * | 12/2002 | Grafinger ............... 623/20.24 |
| 6,506,215 B1 | * | 1/2003 | Letot et al. ............. 623/20.29 |
| 6,558,427 B2 | * | 5/2003 | Leclercq et al. .......... 623/20.33 |
| 6,575,980 B1 | | 6/2003 | Robie et al. |
| 6,632,225 B2 | | 10/2003 | Sanford et al. |
| 6,648,896 B2 | | 11/2003 | Overes et al. |
| 6,972,039 B2 | * | 12/2005 | Metzger et al. .......... 623/20.29 |
| 6,984,249 B2 | * | 1/2006 | Keller .................. 623/20.24 |
| 7,101,401 B2 | * | 9/2006 | Brack .................. 623/20.33 |
| 2003/0130665 A1 | | 7/2003 | Pinczewski et al. |
| 2003/0187452 A1 | | 10/2003 | Smith et al. |
| 2004/0019382 A1 | | 1/2004 | Amirouche |

OTHER PUBLICATIONS

Eckhoff et al., "Three-Dimensional Morphology and Kinematics of the Distal Part of the Femur Viewed in Virtual Reality", *Jnl. Bone & Jt. Surg.*, vol. 85-A Supplement 4, 2003, 97-104.

Howe et al., "Robotics for Surgery," *Annu. Rev. Biomed. Eng.* 1999, 01:211-240.

Mihalko et al., "Comparison of Ligament-Balancing Techniques During Total Knee Arthroplasty," *Jnl. Bone & Jt. Surg.*, vol. 85-A Supplement 4, 2003, 132-135.

Palmer et al., "Total Knee Arthoplasty"[online],[retrieved on Dec. 11, 2003]. Retrieved on from the Internet <URL: http://www.emedicine.com/orthoped/topic347.htm.> (18 pages total).

Rapp, "Electronic Knee Implant May Benefit Future TKR Patients" *Orthopedics Today*, vol. 25, No. 3; (Mar. 2005), p. 14-15.

Ries et al., "Soft-Tissue Balance in Revision Total Knee Arthroplasty," *Jnl. Bone & Jt. Surg.*, vol. 85-A Supplement 4, 2003, 38-42.

Ries et al., "Soft-Tissue Balance in Revision Total Knee Arthroplasty," *Jnl. Bone & Jt. Surg.*, vol. 86-A Supplement 1, 2003, 82-86.

The Gray Sheet, "Knee Implant Surgery Techniques Can Obscure Tech Advances—NIH Panel", FDC Reports "*The Gray Sheet*", Dec. 15, 2003, p. 11.

The Gray Sheet, "Knee Implant Wear Debris, Changing Demographics Weighed by NIH Panel", FDC Reports "*The Gray Sheet*", Dec. 1, 2003, p. 10.

The Gray Sheet, "NIH Consensus: More Knee Replacements Among Young, Old to Grow Market", FDC Reports "*The Gray Sheet*", Dec. 15, 2003, p. 12.

\* cited by examiner

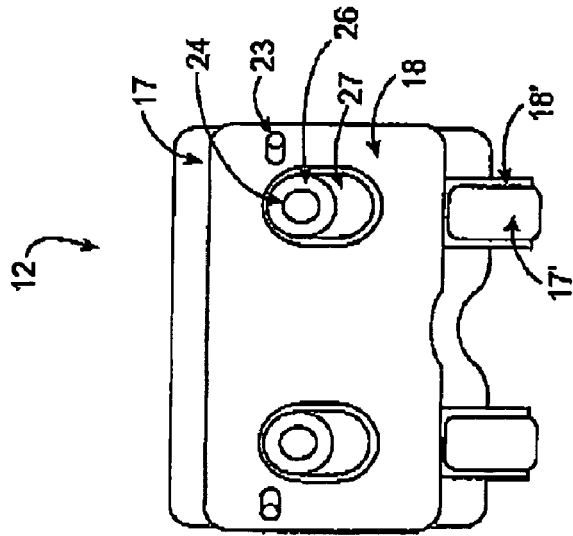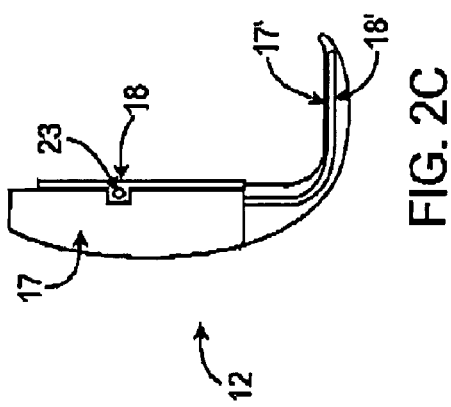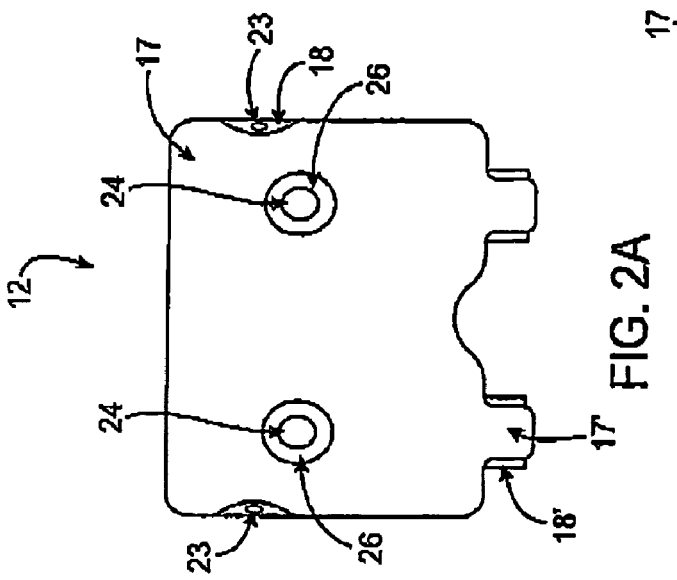

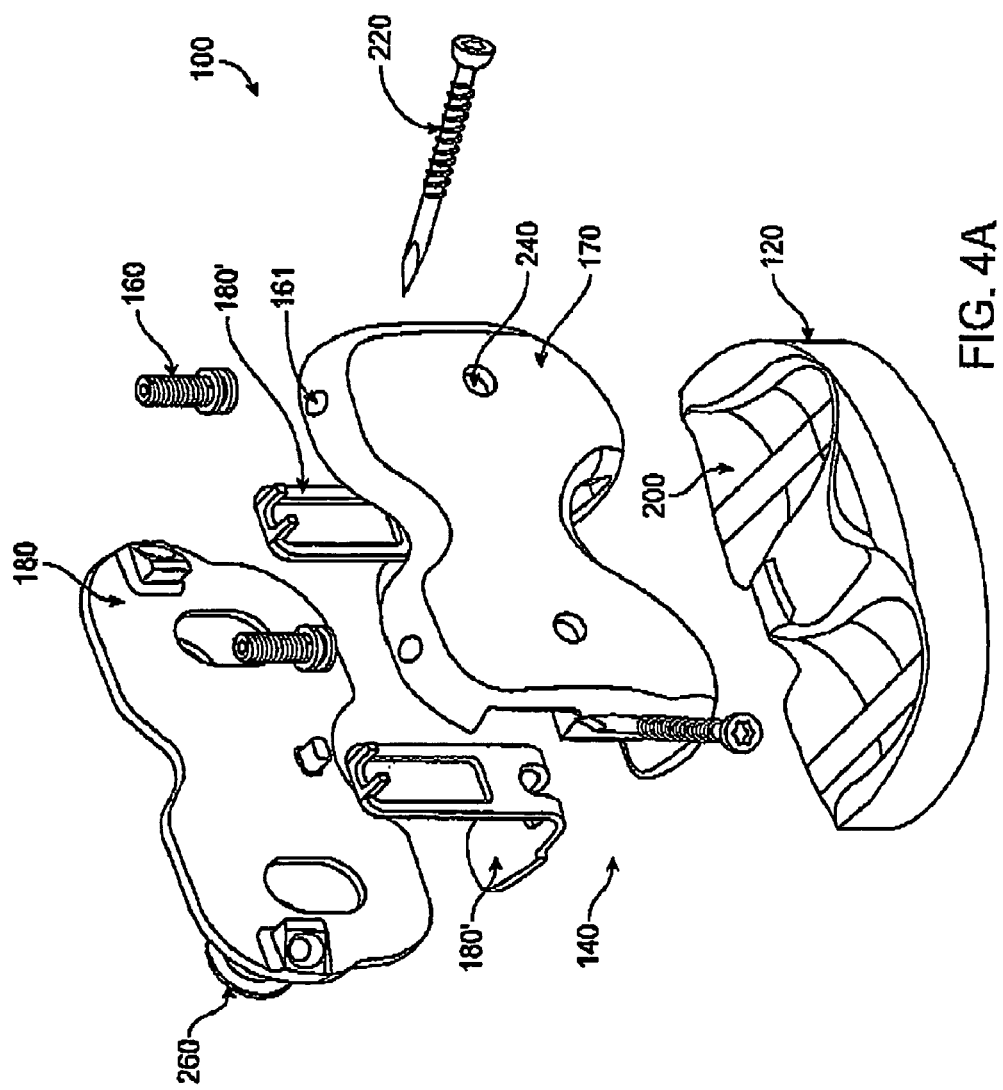

DYNAMIC KNEE BALANCER

BACKGROUND OF THE INVENTION

The present invention relates generally to medical/surgical devices, systems and methods. More specifically, the invention relates to devices, systems and methods for enhancing a knee surgery procedure.

Total knee replacement surgery, also referred to as total knee arthroplasty ("TKA"), is becoming an increasingly important treatment for chronic knee pain and joint dysfunction. A recent panel of the National Institutes of Health at a Consensus Development Conference recognized that approximately 300,000 TKA surgeries are performed annually in the U.S. for end-stage knee arthritis. The NTH panel agreed that although advances have been made in TKA surgical devices and techniques, improved outcomes through further innovations should still be diligently pursued. The panel concluded that techniques for placing artificial knee prostheses, in particular, should be improved to provide better outcomes and reduce wear of the prostheses, to thus reduce the need for repeat TKA surgeries. If advances in TKA continue to be made, the procedure may become more readily available to younger patients, obese patients, and the like, who may need TKA but who do not fall within in the "ideal" age range traditionally defined as between 60 and 75 years old. Improved techniques and devices would also mean enhanced outcomes for all TKA patients, with better functioning of the knee joint and longer useful life of the prosthetic knee.

The knee is generally defined as the point of articulation of the femur with the tibia. Structures that make up the knee include the distal femur, the proximal tibia, the patella, and the soft tissues within and surrounding the knee joint. Four ligaments are especially important in the functioning of the knee—the anterior cruciate ligament, the posterior cruciate ligament, the medial collateral ligament, and the lateral collateral ligament. In an arthritic knee, protective cartilage at the point of articulation of the femur with the tibia has been worn away to allow the femur to directly contact the tibia. This bone-on-bone contact causes significant pain and discomfort. The primary goals of a TKA procedure are to replace the distal end of the femur, the proximal end of the tibia, and often the inner surface of the patella with prosthetic parts to avoid bone-on-bone contact and provide smooth, well-aligned surfaces for joint movement, while also creating a stable knee joint that moves through a wide range of motion.

One of the greatest challenges in TKA surgery is to properly balance ligament tension, especially in the medial and lateral collateral ligaments, through a full range of motion of the knee. The collateral ligaments, which connect the distal femur and proximal tibia on the medial and lateral aspects of the knee, account for much of the stability and movement of the knee. If one of the collateral ligaments is too lax or too tight relative to the other collateral ligament, the knee will typically be unstable, range of motion may be limited, the patella may track improperly, and the femur and/or tibia may wear unevenly, leading to arthritis and pain. Uneven ligament tension after TKA surgery will typically cause joint instability and poor patellar tracking, limited range of motion, and impaired function of the knee, as well as uneven, increased wear of the prosthetic device, which often necessitates repeat surgery. Thus, it is imperative for the short- and long-term success of a TKA procedure to achieve balanced ligament tension in the knee through a full range of motion.

Balancing ligament tension during TKA surgery is complicated by the fact that the natural knee does not operate like a hinge moving about a single axis. The knee exhibits dynamic external rotation of the tibia relative to the femur as the knee moves from its flexed to its fully extended position. This automatic rotation of the tibia occurs in the opposite direction when the knee is flexed from its fully extended position to produce an internal rotation of the tibia relative to the femur. Thus, the natural knee exhibits a rotary laxity that allows the tibia to rotate through a limited internal and external arc, during knee flexion. Additionally, the femur translates anteriorly and posteriorly as the tibia is being flexed about it, bringing yet another movement variable into the equation. Thus, the ligaments of the knee, along with the femur, tibia and patella, create a truly dynamic bio-mechanism, making ligament tension balancing in TKA surgery extremely challenging. Many articles and studies have been devoted to ligament tension balancing in TKA, such as the following: Mihalko, WH et al., "Comparison of Ligament-Balancing Techniques During Total Knee Arthroplasty," Jnl. Bone & Jt. Surg., Vol. 85-A Supplement 4, 2003, 132-135; Eckhoff, D G et al., "Three-Dimensional Morphology and Kinematics of the Distal Part of the Femur Viewed in Virtual Reality, Jnl. Bone & Jt. Surg., Vol. 85-A Supplement 4, 2003, 97-104; and Ries, M D, et al., "Soft-Tissue Balance in Revision Total Knee Arthroplasty," Jnl. Bone & Jt. Surg., Vol. 85-A Supplement 4, 2003, 38-42.

One technique for balancing collateral ligament tension during a TKA procedure involves cutting fibers of one or both ligaments to decrease ligament tension—a technique referred to as "ligament release." Although ligament release is still commonly used, the disadvantage of this technique is that it requires actually cutting ligament tissue, thus weakening the ligament(s) and leaving less room for error if future releases or TKA procedures are required.

Rather than or in addition to ligament release, the components of a total knee prosthesis may be selected and positioned to balance ligament tension. Since the femoral and tibial components of the prosthesis are attached to cut surfaces of the distal femur and proximal tibia respectively, placement and orientation of the bone cuts are also critically important. Typically, the tibial component of the prosthesis is positioned on a flat, horizontal cut surface of the proximal tibia (at a 90 degree angle relative to the long axis of the tibia), and the position and orientation of the tibial component typically do not vary greatly from knee to knee. Therefore, most of the variation in positioning of the total knee prosthesis typically occurs in positioning the femoral component and the femoral bone cuts. The surgeon attempts to make these femoral bone cuts to achieve a position and orientation of the femoral prosthetic component so as to optimally balance ligament tension through a full range of motion of the knee. As with ligament release however, it is often very challenging to position the femoral bone cuts and femoral prosthetic component to provide ideal ligament tension through the range of motion. This is due primarily to the complexity of motion about the knee, as described above, and the difficulty of placing the femoral component so as to maintain desired ligament tension through the full range of motion. Specifically, the rotational, proximal/distal and anterior/posterior orientations and locations of the femoral component are all critical for duplicating the kinematics of the knee.

In a typical TKA procedure, multiple cuts are made to the distal femur before attaching the femoral component of the prosthesis. Most procedures, for example, involve making a distal cut across the distal end of the femur, anterior and posterior cuts, and angled anterior and posterior chamfer cuts to help secure the femoral component solidly in place. In order to effectively and accurately make these resections, orthopedic surgeons typically use a cutting block or cutting guide, used to guide a surgical saw blade or rotary tool, which is temporarily attached to the distal end of the femur. Positioning of such a cutting block, therefore, is crucial to forming well-positioned bone cuts for attachment of the femoral prosthetic component.

A number of devices and techniques have been described that attempt to facilitate ligament balancing during a TKA procedure. Some techniques, such as those described in U.S. Pat. No. 5,733,292, involve trial prosthesis components which are used after femoral and tibial bone cuts are made to assess ligament tension. Some devices, such as those described in U.S. patent application Publication No. 2003/0187452, are used to measure a gap between the distal femur and proximal tibia in extension and to help a surgeon recreate that same gap when the knee is in flexion. Other "gap checking" devices are described in U.S. Pat. No. 6,575,980. Other devices have been developed to help measure an amount of ligament tension or to apply a desired amount of tension to the ligaments. U.S. Pat. No. 4,501,266, for example, describes a knee distraction device for applying a desired amount of tension. Many paddle-like devices have been suggested for applying or measuring tension across a knee joint, such as the devices described in U.S. Pat. Nos. 5,597,379; 5,540,696; 5,800,438; 5,860,980; 5,911,723; and 6,022,377.

One proposed alternative to the cutting block technique for making bone cuts on a distal femur involves the use of robotic surgical systems for making distal femoral bone cuts. With robotic surgery and surgical navigation, a surgical saw blade or bur is still used, but the bone cuts are positioned as a result of fiducial-based or shape-based registration of the patient's anatomy. In fiducial-based approaches, fiducials, or markers are attached to pertinent anatomical structures prior to imaging. During surgery, the markers are exposed, and a sensor system conveys their location to the computer. A wide variety of sensing systems available, including optical trackers, electromagnetic transceivers, articulated probe arms, and ultrasonic and laser range finders. In shape-based approaches, the shapes of anatomical structures are fitted to preoperative image data. The patient measurements can be obtained from a variety of sensing techniques, including tracing curves, scanning distances, or processing images, via one or some of the aforementioned sensing systems. One description of the use of robotic surgery systems in knee surgery procedures is found in Howe, R D, and Matsuoka, Y, "Robotics for Surgery," Annu. Rev. Biomed. Eng. 1999, 01:211-240.

Although some of the devices and techniques described above have helped enhance and facilitate TKA procedures, currently available devices and techniques still have a number of shortcomings. Most importantly, currently available devices do not allow a physician to adjust ligament tension in a knee and also receive positional information based on that adjustment that can be used to facilitate completion of the TKA surgery. For example, many currently available devices are applied only in extension or only in flexion of the knee, or must be removed and replaced when the knee is moved from extension to flexion. Thus, it is difficult or impossible to assess ligament tension through the full range of motion using many currently available devices. Some devices rely on measuring a gap or amount of tension in extension and then recreating the gap or tension in flexion. Again, this does not always result in collateral ligament balance throughout the range of motion. Still other devices are very cumbersome and/or complex. Many include large parts which fit external to the knee joint and necessitate the patella being moved to the side during measurement or other phases of the TKA procedure. Furthermore, current devices typically do not reside primarily within the joint space during a surgical procedure to allow for the natural movements, rotations and translations of the tibia and femur as the knee is flexed through a range of motion. In some techniques, bone cuts are made before ligament balancing is achieved, thus often requiring re-cutting of those same bone cuts. More bone cuts mean more trauma to the patient, a longer recovery period, and less bone to work with if a second TKA is required later in life.

Although robotic surgery may provide a level of improvement over more traditional techniques, it is typically difficult or impossible using current robotic techniques to dynamically mark or register and sense the proper dynamic position to make well-positioned, subsequent bone cuts for attachment of the femoral prosthetic component. Thus, even with robotic systems, it is still challenging to achieve a desired ligament balance to enhance knee stability, range of motion and patellar tracking. These and other shortcomings of currently available devices and methods continue to make ligament balancing, and specifically collateral ligament balancing, one of the most challenging aspects of TKA surgery.

Therefore, a need exists for improved devices, systems and methods for enhancing TKA surgery and specifically for dynamically balancing ligaments during TKA to improve range of motion, stability, and patellar tracking of the prosthetic knee joint. Ideally, such devices would help a surgeon balance ligaments dynamically, through a full range of motion of the knee, allowing for the natural rotation of the tibia and the natural translation of the femur while the tibia is being flexed about it. Also ideally, such devices and methods would allow a surgeon to achieve a desired ligament tension balance before committing to and making final bone cuts to the femur. Such devices would also ideally be simple to use in conjunction with cutting guides, saw blades or burs, and robotic and navigational systems, preferably allowing the patella to remain in place during assessment of ligament tension. At least some of these objectives will be met by the present invention.

BRIEF SUMMARY OF THE INVENTION

The present invention provides devices, systems and methods for enhancing knee surgery procedures, and more specifically total knee replacement procedures (total knee arthroplasty, "TKA"). Various embodiments generally include a stationary femoral member for removably attaching to a distal femur and an adjustable femoral member coupled with the stationary member for providing adjustability. The adjustable member is movably couplable with a tibial member engaged with the proximal tibia of the knee, allowing for the natural movements, rotations and translations of the tibia and femur to take place as the knee is flexed and/or extended through a range of motion, resulting in dynamic ligament tension balancing through a range of motion of the knee.

The adjustable femoral member is adjustable to adjust tension in at least one ligament of or adjacent the knee. Typically, the adjustable member is separately adjustable on either side to adjust tension in the lateral and/or medial collateral ligaments adjacent the knee. When the adjustable femoral member is adjusted to adjust ligament tension, one or more positioning features of the adjustable member provide positioning information to help position and/or orient a cutting guide, surgical saw blade, bur, mill, surgical navigation system, robotic surgical system or the like. This positioning information is then typically used to make subsequent bone cuts to the distal femur, or to otherwise mill or shape the distal femur, so that when a femoral prosthetic component is applied, the knee has a desired stability, range of motion and/or patellar tracking. Devices and methods of the invention thus help to dynamically balance ligament tension in a knee during TKA surgery, without requiring ligament releases, to provide for a dynamically balanced knee after the surgery is complete.

For purposes of the present description, the terms "ligaments of the knee," "ligaments in the knee," "ligaments adjacent the knee," and the like are all synonymous and all refer generally to any ligaments within the knee joint space, around the knee, adjacent the knee, or near the knee. These terms typically refer to the ligaments that assist in the functioning of the knee, and often the ligaments referred to are the medial collateral ligament, the lateral collateral ligament, the anterior cruciate ligament and the posterior cruciate ligament. Although the following description focuses on the use of various embodiments in TKA surgical procedures, these and/or other embodiments may suitably be used to facilitate other knee surgery procedures, other orthopedic joint surgery procedures and the like.

That being said, in one aspect of the present invention, a device for enhancing a surgical procedure on a knee includes at least one stationary femoral member for removably attaching to a distal femur and at least one adjustable femoral member movably coupled with the stationary member to adjust tension in at least one ligament of or adjacent the knee. The adjustable femoral member includes at least one positioning feature that moves relative to the distal femur as the adjustable femoral member is adjusted and thus identifies at least one position on the distal femur for facilitating completion of the surgical procedure to enhance at least one of range of motion, stability and patella tracking of the knee. Furthermore, the adjustable femoral member is movably couplable with at least one tibial member engaged with a proximal tibia to allow the knee to be moved through a range of motion without removing the femoral and tibial members.

In some embodiments the stationary femoral member is engageable with a cut surface at the distal end of the distal femur. Similarly, in some embodiments the tibial member is engageable with a cut surface at the proximal end of the tibia. Typically, the adjustable femoral member is separately adjustable on a medial side and a lateral side of the femoral member to adjust tension in the at least one ligament. In some embodiments, adjusting on one side relative to the other side causes the adjustable femoral member to rotate relative to the anterior and posterior aspects of the distal femur.

Adjustment of the at least one adjustable member may be accomplished via any suitable adjustment device, components, techniques and the like. For example, in some embodiments the adjustable member includes at least one lateral adjustment member for adjusting a lateral portion of the adjustable member and at least one medial adjustment member for adjusting a medial portion of the adjustable member. The adjustment members may comprise screws, pins, levers, spring-loaded members or any other suitable device or devices for conferring adjustability. In other embodiments, the adjustable femoral member may be partially or completely self-adjusting, for example via one or more spring-loaded or shape memory self-adjusting members or the like. In still other embodiments, the at least one adjustable femoral member comprises multiple pre-adjusted femoral members, each pre-adjusted femoral member conferring different amounts of ligament tensioning and balancing about the knee. A surgeon may choose any one of the pre-adjusted femoral members for balancing ligament tension, and may try more than one pre-adjusted member before deciding which to use. Thus, by the terms "adjustable," "adjustable femoral member," "adjustability" and the like it is meant that one or more members may be used to adjust ligament tension in the knee. In various embodiments, adjustability may be achieved via one or more adjustable members, self-adjusting members, interchangeable pre-adjusted members, or any other suitable devices.

In various embodiments, a device for enhancing knee surgery may be used interchangeably for either a left knee or a right knee. In other words, some embodiments of a knee surgery device are not typically specific to either a left knee or a right knee, although such left-side-specific/right-side-specific devices are contemplated. Thus, because the typical knee balancing device of the present invention is used on either knee, the terms "medial" and "lateral" should not be interpreted as limiting a device to use for either a left knee or a right knee. For example, an adjustment member that is oriented laterally relative to a right knee will be oriented medially relative to a left knee.

In some embodiments, the at least one adjustable femoral member comprises at least one distal femoral portion for emulating the distal condylar surface of the femur and at least one posterior condylar portion to emulate posterior condylar surfaces of the femur. In some embodiments, the at least one posterior condylar portion comprises a medial femoral posterior condylar portion and a lateral femoral posterior condylar portion. In one embodiment, the distal femoral portion, the medial femoral posterior condylar portion and the lateral femoral posterior condylar portion are all one piece or extrusion. In other embodiments, these portions may be multiple, coupled parts. The distal and posterior condylar portions allow the femoral member to movably engage with the tibial member to allow the knee to be moved through a range of motion while the device is engaged with the knee.

In some embodiments, the distal femoral portion and posterior condylar portions of the adjustable femoral member are movably couplable with one or more complementary depressions in the tibial member. For example, the posterior condylar members may comprise a medial femoral posterior condylar member slidably couplable with a medial depression of the tibial member and a lateral femoral posterior condylar member slidably couplable with a lateral depression of the tibial member.

In some embodiments, the at least one stationary femoral member comprises at least one distal femoral plate for coupling the distal femoral portion of the adjustable femoral member to the distal femur and at least one posterior condylar member wrapping around from the distal femoral portion to contact at least part of a medial posterior femoral condyle and a lateral posterior femoral condyle of the distal femur. Optionally, the posterior condylar members comprise a medial femoral posterior condylar member and a lateral femoral posterior condylar member. Often, in such embodiments, the medial femoral posterior condylar portion of the adjustable femoral member is adjustable relative to the medial side of the stationary femoral member, and the lateral femoral posterior condylar portion of the adjustable femoral member is separately adjustable relative to the lateral side of the stationary femoral member. In some embodiments, the distal femoral portion and posterior condylar members of the stationary femoral member may comprise one piece or extrusion. In alternative embodiments, the stationary femoral member may comprise multiple coupled parts.

The adjustable member may be adjustable in any number of ways, but in one embodiment it is adjustable relative to the stationary femoral member to separately adjust tension in the medial collateral ligament and/or the lateral collateral ligament of the knee. In making such adjustments, tension of other ligaments, such as the anterior and/or posterior cruciate ligaments, may also be adjusted. In some embodiments, the adjustable femoral member self-adjusts relative to the stationary femoral member to separately adjust tension in the medial collateral ligament, lateral collateral ligament and/or other ligaments.

When the adjustable femoral member is adjusted to adjust and balance ligament tension, the at least one positioning feature moves relative to the distal femur and the stationary member. The post-adjustment position of the positioning feature(s) provides positional information which may then be used for completing the TKA procedure. For example, such information may be used to position a cutting guide on the distal femur for making subsequent bone cuts, to make the bone cuts themselves, to apply the femoral prosthetic component to the distal femur, and/or the like. The positioning features themselves may comprise any of a number of different features, such as but not limited to one or more apertures, drill bit guides, surface markers, surface features, measurement devices, embedded markers, fiducials, transponders, transceivers and/or sensors.

In one embodiment, for example, two or more apertures act as the positioning features. In some embodiments, these apertures rotate relative to the distal femur when the adjustable femoral member is adjusted. Additionally or alternatively, the apertures may move in an anterior and/or posterior direction relative to the distal femur. The apertures may provide information in a number of different ways. For example, they may act as drill bit guides to guide the drilling of holes into the distal femur for attachment of a cutting guide. Typically, such apertures extend through the adjustable member and through apertures in the stationary femoral member to the distal femur to allow for passage of the drill bit. Alternatively, fiducials, sensors, transmitters, markers or the like may be disposed in the apertures and may send or receive signals or act as markers for use by external devices. In one embodiment, for example, a robotic surgical system and/or a navigational system may use the position of such fiducials, sensors, markers or the like to help guide a surgical saw blade, bur or the like to shape the distal femur. Optionally, the apertures may be positioned slightly asymmetrically on the adjustable member to provide for a built-in desired flexibility in the ligaments, to achieve enhanced range of motion, stability, and patellar tracking of the prosthetic knee joint, when the surgical procedure is completed. In another embodiment, the at least one adjustable femoral member may be asymmetrically oriented relative to the stationary member to provide built-in desired flexibility in the ligaments, to achieve enhanced range of motion, stability, and patellar tracking of the prosthetic knee joint, when the surgical procedure is completed.

Any other suitable positioning feature or combination of features may be included in the adjustable femoral member, including any feature now known or hereafter discovered. Furthermore, the positional information derived from such positioning features may be generated and used in any suitable fashion. For example, positional features may act as markers which may be queried by an external system, such as a navigational or robotic system. Positional information may then be generated and/or processed via a computer and data regarding post-adjustment positions, pressures, ligament tensions at various points in a range of motion may be provided to a user and/or to a robotic surgery device. Positional information may also be provided by mechanical means such as torque applied and adjusted to the adjustment mechanism of the adjustable member. Generally, any suitable positioning feature may be used and any positional information, ligament tension information and/or the like may be generated by various embodiments of the invention.

Typically, the at least one tibial member is engageable with a cut surface of the proximal tibia. Examples of tibial members include but are not limited to shims, paddles, plates, bars, platforms and rods. In a preferred embodiment, a plurality of tibial shims are provided, having different thicknesses or heights, and any one of the plurality of shims may be selected for engaging with the cut surface of the proximal tibia to provide a desired amount of tension in the ligaments. Optionally, the at least one tibial member may further comprise a plate for removably attaching to the cut surface of the proximal tibia, disposed between the cut surface and the selected tibial shim.

In one embodiment, the femoral and tibial members are movably coupled via force provided by at least one ligament adjacent the knee. More specifically, in one embodiment the femoral and tibial members are coupled only via force provided by ligament force. This coupling of the femoral and tibial members by ligament force may be described as "dynamic" coupling. Such coupling helps allow ligament tension to be balanced with a device that resides primarily within the joint space and also allows for the natural movements, rotations and translations of the tibia and femur to take place as the knee is flexed through a range of motion, resulting in dynamic ligament tension balancing through a range of motion of the knee. Thus, in one embodiment the femoral and tibial members, when engaged with the distal femur and proximal tibia respectively, are disposed primarily within a joint space between the distal femur and the proximal tibia. In such embodiments, a patella of the knee may remain approximately in its anatomical position while the femoral and tibial members are engaged and the knee is moved through the range of motion during the TKA procedure. The movable coupling of the femoral and tibial members allows for flexion and extension through the range of motion. By "range of motion," it is meant that the knee is moved from extension to flexion and/or from flexion to extension. In some embodiments, the range of motion comprises a range from approximately full extension of the knee to approximately full flexion of the knee. In other embodiments the range of motion may be narrower.

Components of the femoral and tibial members may be manufactured from any materials or combinations of materials known in the art or hereafter discovered. For example, in one embodiment either or both the stationary femoral member and the adjustable femoral member comprise at least one material selected from the group consisting of plastics, composites, aluminum, stainless steel, composite, cobalt-chrome, titanium, and other metals. In some embodiments, the femoral and/or tibial members may further include at least one grasping member for facilitating placement and/or removal.

In another aspect of the present invention, a system for enhancing a surgical procedure on a knee comprises at least one femoral member removably engageable with a distal femur and at least one tibial member removably engageable with a proximal tibia and movably couplable with the femoral member to allow the knee to be moved through a range of motion without removing the femoral and tibial members. The femoral member includes at least one stationary member for attaching to the distal femur and at least one adjustable femoral member movably coupled with the stationary member to adjust tension in at least one ligament of or adjacent the knee. The adjustable femoral member includes at least one positioning feature that moves relative to the distal femur as the adjustable femoral member is adjusted and thus identifies at least one position on the distal femur for facilitating completion of the surgical procedure to enhance at least one of range of motion, stability and patella tracking of the knee. Such a system may include any of the features described above.

As with the various embodiments of the devices described above, adjustment of the at least one adjustable member may be accomplished by any suitable means. Thus, in various embodiments of the system the at least one adjustable femoral member may include one or more adjustable members, self-adjusting members, interchangeable pre-adjusted members, or any other suitable devices for conferring adjustability.

In still another aspect of the present invention, a method for facilitating a surgical procedure on a knee involves: engaging at least one femoral member with a distal femur to movably couple with a tibial member engaged with a proximal tibia, the femoral member comprising at least one stationary member and at least one adjustable member; moving the knee; and adjusting the adjustable femoral member to apply tension to at least one of the ligaments of or adjacent the knee, thus moving at least one positioning feature of the adjustable femoral member relative to the distal femur to identify at least one position on the distal femur for facilitating completion of the surgical procedure.

Typically, though not necessarily, the tibial member is engaged with a cut surface of the proximal tibia, and the femoral member is engaged with a cut surface of the distal femur. As mentioned above, in some embodiments the tibial and femoral members are engaged primarily within a joint space between the cut surfaces of the proximal tibia and the distal femur and are movably coupled via force provided by the at least one ligament adjacent the knee. This coupling of the femoral and tibial members by ligament force may be described as "dynamic" coupling. Such coupling helps allow ligament tension to be balanced with a device that resides primarily within the joint space and also allows for the natural movements, rotations and translations of the tibia and femur to take place as the knee is flexed through a range of motion, resulting in dynamic ligament tension balancing through a range of motion of the knee.

In some embodiments, engaging the tibial member comprises selecting the tibial member from a plurality of tibial members with different dimensions, the selected tibial member having dimensions to apply a desired amount of tension to the at least one ligament. Engaging the femoral member, in some embodiments, involves attaching a stationary portion of the femoral member to the distal surface of the femur, with an adjustable portion of the femoral member being coupled with the stationary portion. In some embodiments, moving the knee comprises sliding at least one distal femoral condylar and posterior condylar member of the femoral member along at least one complementary depression in the tibial member. More generally, moving the knee may involve sliding the tibial member along the femoral member.

In some embodiments, moving the knee may involve moving from approximately full extension to approximately full flexion. Alternatively, moving the knee may involve moving from approximately full flexion to approximately full extension. In some embodiments, the knee may be moved between extension and flexion more than once, either before, after or during adjustment of the adjustable member. For example, in some embodiments the method may further involve moving the knee after the adjustment step and further adjusting the adjustable femoral member. Any combination of knee movements and adjustments is contemplated within the scope of the present invention. For example, a method may involve moving the knee through a range of motion to help determine the desired ligament tension balance in the knee during the range of motion. In some embodiments, at least the moving and adjusting steps are performed with the patella of the knee located approximately its anatomic position over the knee.

Adjusting the adjustable femoral member, in some embodiments, involves adjusting tension in at least one of a medial collateral ligament and a lateral collateral ligament. Sometimes adjusting the adjustable femoral member comprises enlarging a joint space between at least part of the distal femur and proximal tibia to apply tension to at least one of the ligaments. Enlarging the joint space may involve enlarging the space primarily at a medial side of the knee or primarily at a lateral side of the knee in various embodiments. Typically, enlarging the space applies tension to the medial collateral ligament, the lateral collateral ligament or both. In some embodiments, adjusting the adjustable femoral member comprises moving an adjustable portion of the femoral member relative to a stationary portion of the femoral member. For example, adjusting the adjustable femoral member may involve adjusting at least one adjustment member on the adjustable femoral member. In one embodiment, for example, one or more screws may be turned to adjust the adjustable femoral member.

In some embodiments, adjusting the adjustable femoral member causes at least one positioning feature on the femoral member to be oriented to the distal end of the femur, the positioning feature(s) helping determine a position for applying a cutting guide to the distal femur, for orienting a surgical navigation system sensor, for locating and or making subsequent bone cuts, or the like. In some embodiments, for example, the at least one positioning feature comprises one or more apertures for guiding a drill bit for forming one or more drill holes used to attach a cutting guide, for dynamically orienting a bone cutting device, for dynamic placement of fiducials or markers to orient a surgical navigation system sensor to the distal end of the femur, or the like. In some embodiments, the least one aperture comprises at least two apertures, and adjusting the adjustable femoral member causes the at least two apertures to rotate relative to one another over the distal end of the femur. For example, the apertures may rotate about an axis approximately corresponding to a long axis of the distal femur. Alternatively or additionally, adjusting the adjustable femoral member may cause the at least one aperture to move in an anterior or posterior direction relative to the distal femur. Of course, as described above, any suitable positioning features may be included on the adjustable member, and any methods for acquiring or using positional information may be employed in various embodiments.

In some embodiments, the method further involves: placing at least one hole or slot in the distal end of the femur, using the at least one aperture to guide a tool bit; removing the adjustable femoral member from the distal femur; using the at least one hole for attaching a cutting guide to the distal end of the femur; and making at least one cut on the distal end of the femur. Optionally, such a method may further include attaching a femoral prosthesis component to the cut distal end of the femur and attaching a tibial prosthesis component to a cut surface of the proximal tibia. In alternative embodiments, the method may further include sending one or more signals from the at least one positioning device to a distal femur cutting device and cutting the distal femur with the cutting device, based on the signal(s). Such signals, for example, may be used as part of a navigational system and/or robotic surgical system.

Further details of these and other embodiments are described more fully below, with reference to the attached drawing figures.

BRIEF DESCRIPTION OF THE DRAWINGS

FIG. 2A is a frontal view of a knee balancing device according to one embodiment of the present invention;

FIG. 2B is a rear view of the knee balancing device shown in FIG. 2A;

FIG. 2C is a side view of the knee balancing device shown in FIGS. 2A and 2B;

FIG. 4A is a front-perspective, exploded view of a knee balancing device according to one embodiment of the present invention.

DETAILED DESCRIPTION OF THE INVENTION

As discussed above, the present invention provides devices, systems and methods primarily intended for enhancing total knee arthroplasty (TKA) surgical procedures. Although these devices, systems and methods are used primarily in TKA, however, some embodiments may be used to enhance other knee surgery procedures or surgical procedures on other joints, such as an elbow joint.

That being said, devices, systems and methods of the invention generally help a surgeon to balance ligament tension in a knee during a TKA procedure and thereby help the surgeon perform the TKA so as to achieve a desired ligament balance when the surgery is complete. Devices, systems and methods of the invention generally facilitate dynamic balancing of ligaments of the knee, such that these ligaments remain balanced through a range of motion about the knee. Oftentimes, such dynamic balancing helps create a prosthetic knee that has a desirable level of stability, patellar tracking and range of motion.

Figure 1A:
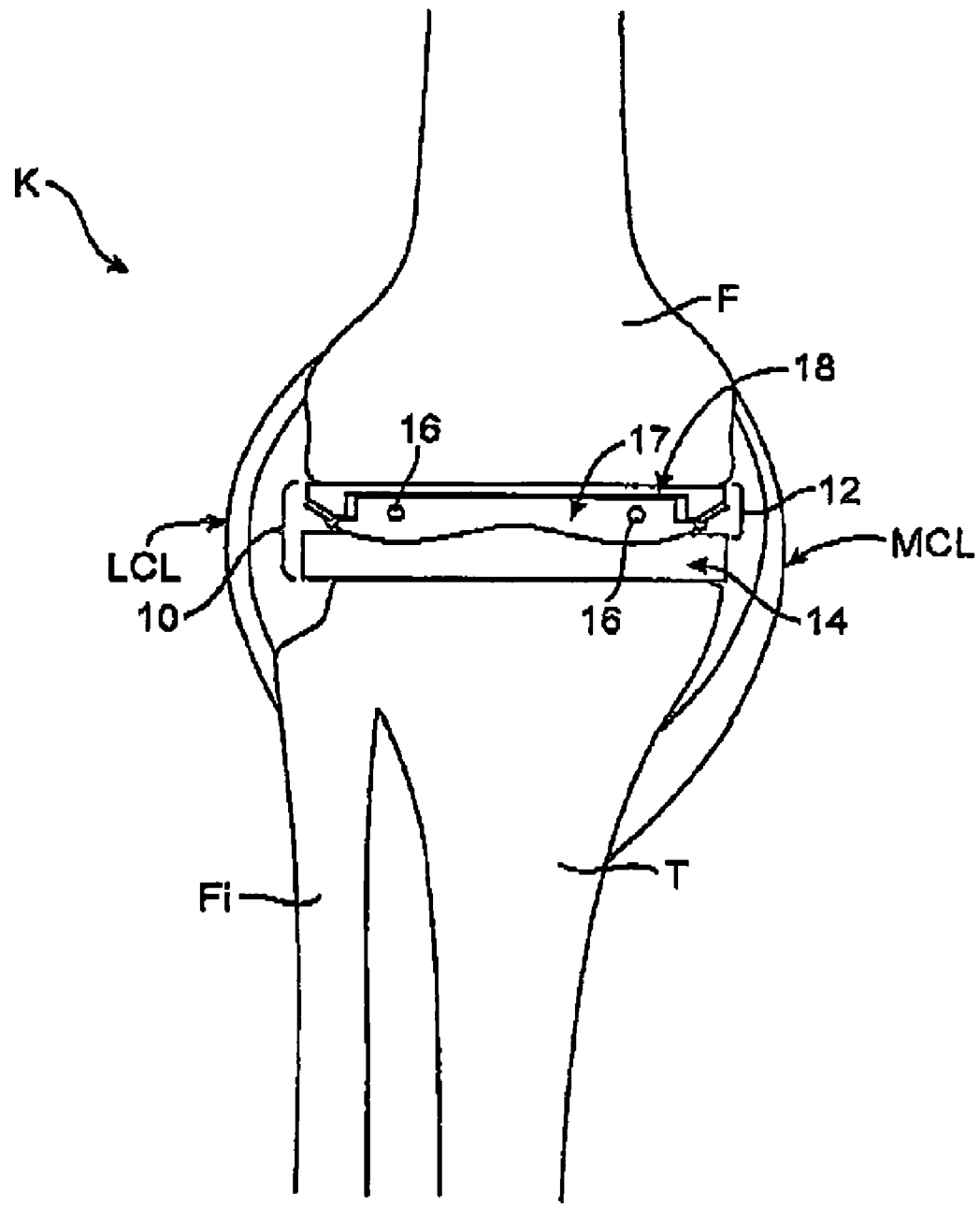
FIG. 1A is a frontal view of a knee in extension, with a knee balancing device according to one embodiment of the invention in place within the knee joint.

With reference now to FIG. 1A, a frontal view of a right knee K is shown in extension, with a knee balancing system 10 in place within the knee joint space. The anatomical components of the knee K that are pertinent to this description include a distal femur F, a proximal tibia T, a medial collateral ligament MCL, and a lateral collateral ligament LCL. (Also labeled is the proximal fibula Fi, to which the LCL attaches.) The knee K is shown without a patella, medial collateral ligament or lateral collateral ligament, for clarity, but many embodiments may be used while the patella is in its anatomical position on the anterior aspect of the knee K. In FIG. 1A, a portion of the distal end of the distal femur F and a portion of the proximal end of the proximal tibia T have been cut or shaved off, to create level surfaces on which to place femoral member 12 and a tibial member 14, respectively, of dynamic knee balancing system 10. In various embodiments, a knee balancing device may be provided as only a femoral member, for example to be used with off-the-shelf tibial trial inserts. In other embodiments, knee balancing system 10, comprising femoral member 12 and tibial member 14 may be provided.

In the embodiment shown, femoral member 12 is adjustable to adjust tension in the MCL, the LCL, or both. Adjustability may be achieved by any suitable means, some of which are described in more detail above and below. In one embodiment, for example, one or more adjustment members 16, which may comprise screws, pins, levers, spring-loaded mechanisms, shape memory materials or the like, are coupled with femoral member 12 to provide adjustability. In some embodiments, adjustment members 16 may be used for separately adjusting femoral member 12 on either side to separately adjust tension in the MCL or the LCL.

In general, femoral member 12, tibial member 14 and any of their component parts may be manufactured from any suitable material now known or hereafter discovered. For example, femoral member 12 and/or tibial member 14 in some embodiments may be manufactured from one or more plastics, composites and/or metals, such as aluminum, stainless steel, composite, cobalt-chrome, titanium, or the like. These or any other suitable material(s) and combinations of materials may be used in various embodiments.

As shown in FIG. 1A and subsequent figures, knee balancing system 10 is typically disposed primarily within the joint space of knee K during a TKA surgery, thus providing for more convenient manipulation of the knee, anatomical positioning of the patella during surgery and the like. In alternative embodiments, however, a knee balancing device or system could be engaged with the knee at a location external to the knee joint. For example, in one embodiment the device may comprise an externally applied frame that performs the same functions as the devices described herein. In such embodiments, some or all of the knee balancing device may be located external to the knee joint, thus not fitting within the knee joint space during the surgical procedure.

Figure 1B:
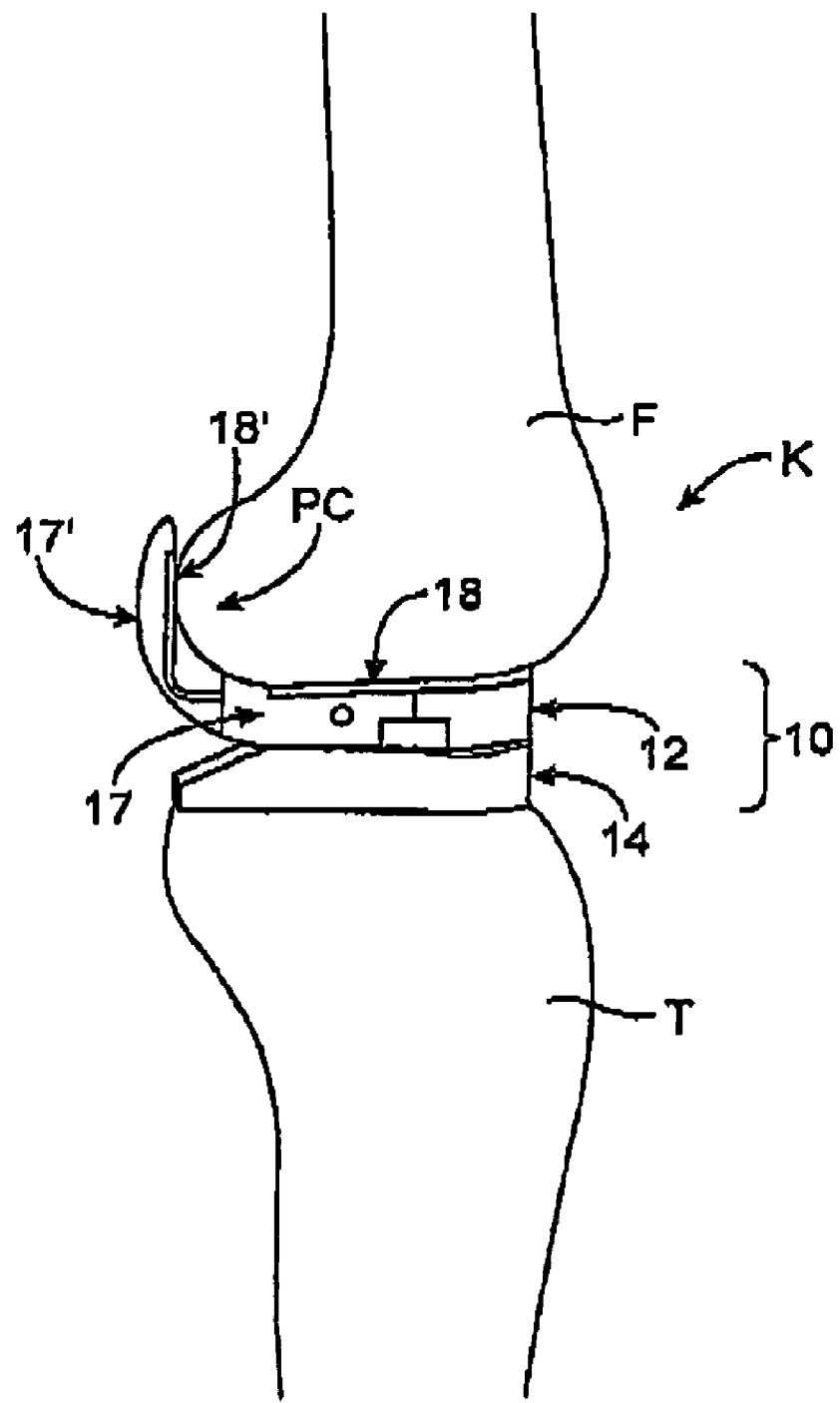
FIG. 1B is a side view of the knee in extension and knee balancing device shown in FIG. 1A.

Referring now to FIG. 1B, the knee K is shown from a side view. In this and subsequent figures, the collateral ligaments MCL and LCL, other ligaments such as the posterior cruciate ligament PCL, and the fibula Fi are removed for clarity. As is visible in this view, femoral member 12 suitably comprises a stationary femoral member 18 an adjustable femoral member 17. Stationary femoral member 18 has a base which is typically removably attached to a surface of the distal femur F, often a cut surface at the distal end of the distal femur F, and adjustable femoral member 17 is coupled with stationary femoral member 18. Stationary femoral member 18 includes at least one stationary posterior condylar member 18' disposed at a substantially right angle relative to its base and extending posteriorly therefrom to contact at least one of the medial and lateral posterior condyles PC of the distal femur F. Typically, stationary femoral member 18 includes two stationary posterior condylar members 18', one for each posterior condyle PC. Similarly, adjustable femoral member 17 has a base, the surface of which is typically configured to contact the surface of tibial member 14 when the knee is in extension, and suitably includes one or more (preferably two) adjustable posterior condylar members 17' disposed at a substantially right angle relative to the base and extending posteriorly therefrom to emulate the two posterior condyles PC. As is described more fully below, posterior condylar members 17',

18' allow femoral member 12 to be adjusted to balance ligament tension in the knee K and also allow knee balancing system 10 to remain in place within the joint space while the knee K is moved through a range of motion. In various embodiments, stationary femoral member 18 and stationary posterior condylar members 18' may be either multiple, couple parts or may be one piece or extrusion. Similarly, adjustable fenioral member 17 and adjustable posterior condylar members 17' are all one piece or extrusion in some embodiments, but may alternative comprise multiple coupled parts.

Typically, adjustable femoral member 17 is movably engageable with tibial member 14 to allow knee balancing system 10 to remain in place within the knee joint space while the knee K is moved through a range of motion. In some embodiments, such as the one shown in FIG. 1 and subsequent figures, adjustable femoral member 17 and tibial member 14 are movably engaged with one another via force applied by the ligaments of the knee K, especially the MCL and LCL. In other words, femoral member 12 and tibial member 14 are two separate components which are brought together into a movable/slidable coupling by ligament force. Such coupling of adjustable femoral member 17 and tibial member 14 via ligament force provides for dynamic balancing of the knee through a full range of motion. In various alternative embodiments, ligament force may not be used for coupling femoral member 12 with tibial member 14, and instead a passive mechanical coupling may be used.

Figure 1C:
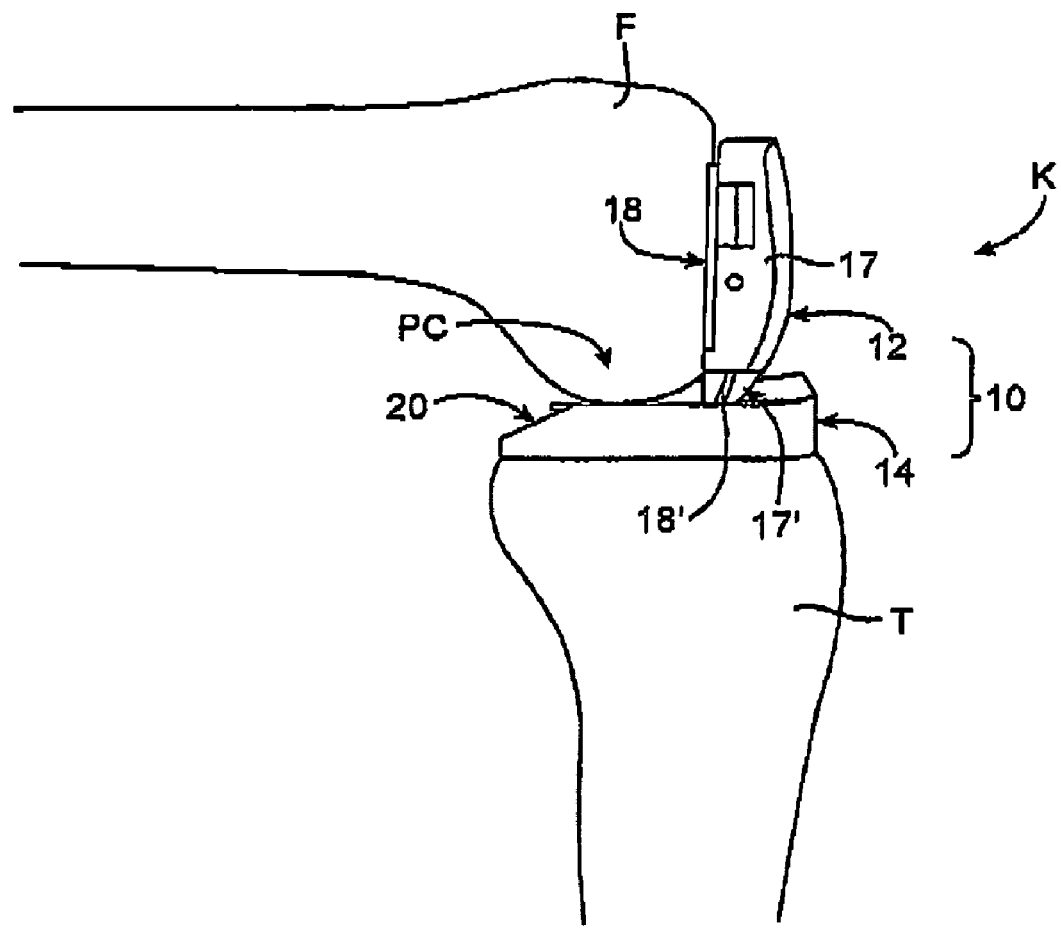
FIG. 1C is a side view of the knee and knee balancing device shown in FIGS. 1A and 1B, with the knee in a position of flexion.

With reference now to FIG. 1C, knee balancing system 10 is shown with the knee K in flexion. It can be seen here that stationary posterior condylar member 18' and adjustable posterior condylar member 17' are slidably engageable with complementary grooves 20 on tibial member 14. Thus, knee balancing system 10 is movable/slidable through approximately a full range of motion of the knee K, from full extension to full flexion and vice versa.

Figure 1D:
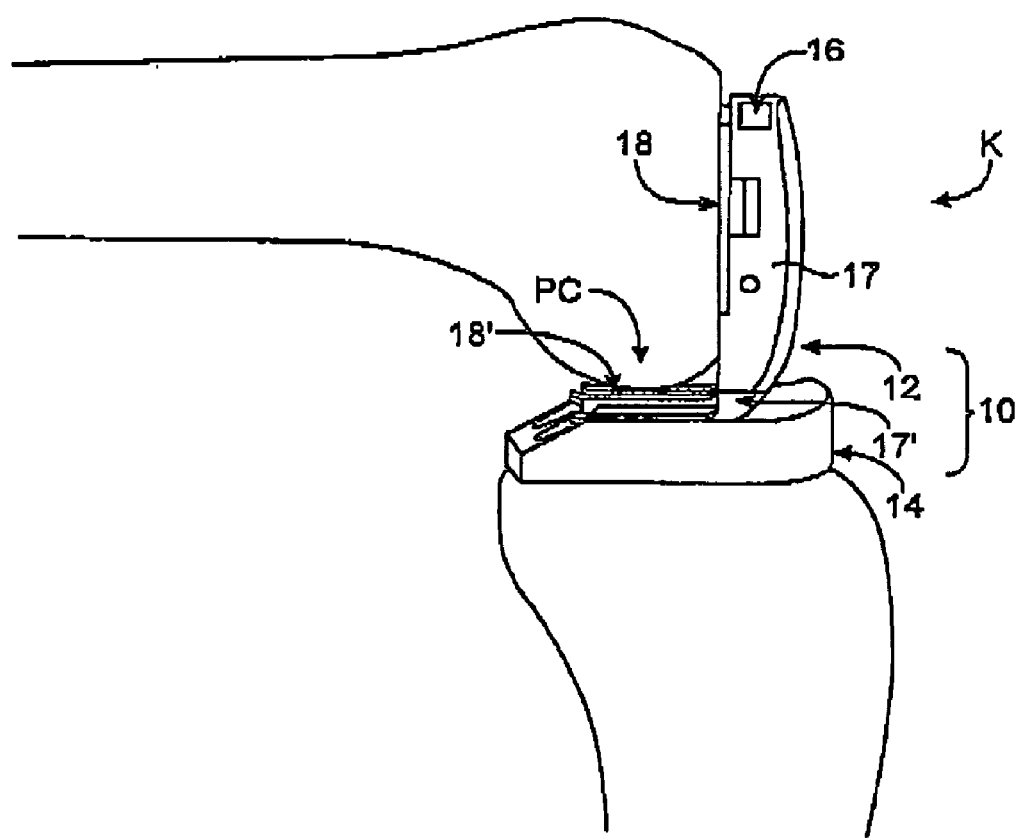
FIG. 1D is a side view of the knee and knee balancing device shown in FIGS. 1A-1C, with the knee balancing device adjusted to achieve a desired ligament tension balance according to one embodiment of the invention.

Referring to FIG. 1D, knee balancing system 10 is shown after an adjustment has been made to adjustable femoral member 17. In one embodiment, adjustable femoral member 17 is separately adjustable on either side to separately adjust tension in the MCL and/or the LCL. Such adjustment(s) may be achieved by any suitable means, such as manual adjustment via a screw or other adjustment member, self-adjustment via a spring-loaded mechanism, or the like. In the embodiment shown, adjustment member 16 is adjusted to move adjustable femoral member 17 relative to stationary femoral member 18. As adjustment member 16 is adjusted, adjustable femoral member 17 rotates relative to stationary femoral member 18, thus causing adjustable posterior condylar member 17' to move away from stationary posterior condylar member 18'. This movement creates a larger joint space on the side of adjustment, thus tightening the collateral ligament on that side. Meanwhile, the distal femoral portion of adjustable femoral member 17 has rotated relative to the distal femoral portion of stationary femoral member 18, approximately about the long axis of the femur F. If adjustment members 16 on both sides of adjustable femoral member 17 are adjusted in the same direction, adjustable femoral member 17 may be caused to move anteriorly or posteriorly relative to stationary femoral member 18. Thus, adjustable femoral member 17 may be adjusted rotationally as well as in an anterior/posterior orientation.

Figure 1E:
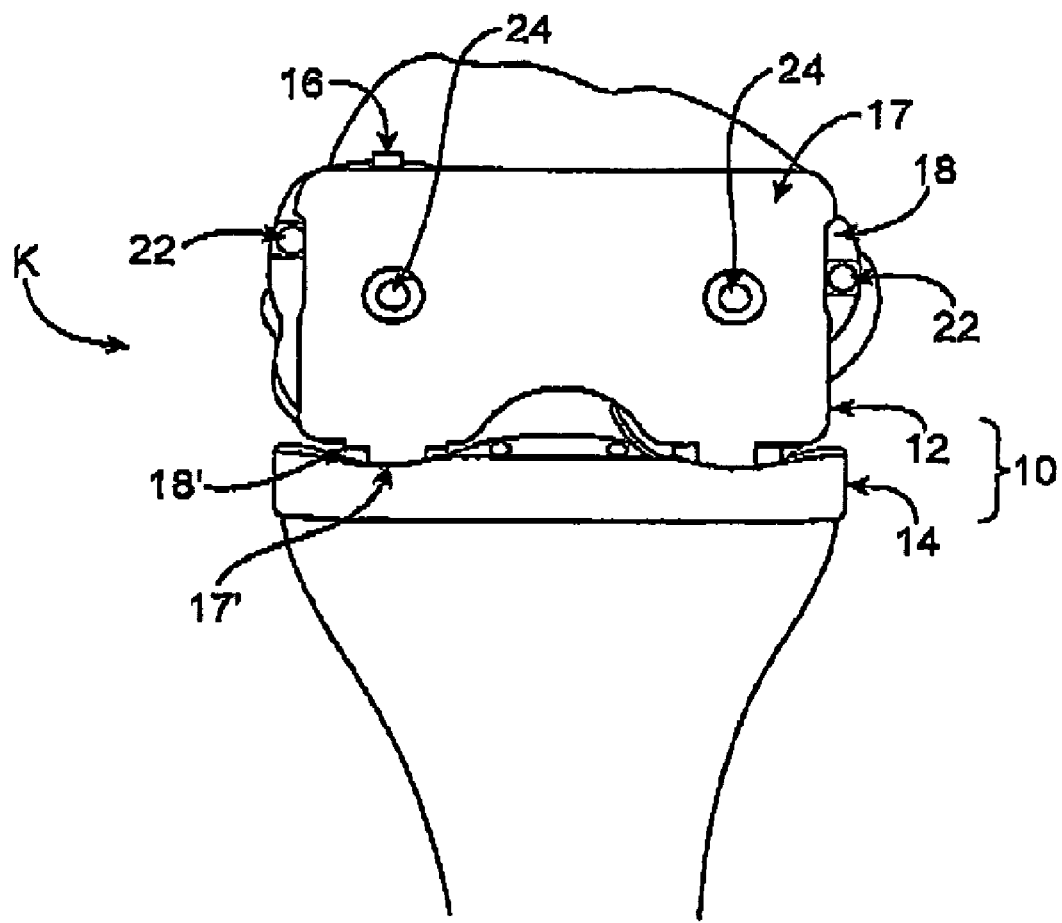
FIG. 1E is a frontal view of the knee and knee balancing device shown in FIGS. 1A-1D, with the knee balancing device adjusted to achieve a desired ligament tension balance according to one embodiment of the invention.

With reference now to FIG. 1E, the knee K and knee balancing system 10 of FIG. 1D is shown in frontal view. Here it can be seen that adjustment of adjustment member 16, on the lateral side of the distal femur F, has caused adjustable posterior condylar member 17' on the lateral side to move away from stationary posterior condylar member 18' on the lateral side, thus increasing the height of the joint space on the lateral side and rotating adjustable femoral member 17 slightly, relative to the distal femur. Adjustable femoral member 17 includes at least one positioning feature for providing positional information for facilitation the TKA procedure. As described above, the positioning feature(s) may include any of a number of different features, such as apertures, surface markers, embedded markers, fiducials, transmitters, transponders, transceivers, sensors and/or the like. These positioning features provide positional information that can then be used to facilitate the TKA procedure. For example, apertures may act as drill bit guides for drilling holes to apply a cutting guide to the femur F to make subsequent bone cuts. In another embodiment, apertures may contain fiducials or markers to provide information to a navigational system and/or robotic surgical system for positioning subsequent bone cuts or otherwise shaping the distal femur F via milling, burring or the like. Various embodiments have been fully described above, and any suitable positioning features and positional information may be used in various embodiments.

In the embodiment shown, adjustable femoral member 17 includes two apertures 24 as positioning features. Apertures 24 extend through adjustable femoral member 17 and also through stationary femoral member 18 such that apertures 24 may be used to guide a drill bit to form holes in the distal femur F. Of course, as just discussed, apertures 24 can serve any of a number of other functions, such as carrying fiducials, sensors, markers or the like. In some embodiments, corresponding apertures in stationary femoral member 18 are large enough to allow for movement of apertures 24 on adjustable femoral member 17 such that apertures 24 extend all the way to the cut surface of the distal femur F. When apertures 24 are used to drill holes for a cutting guide, the balancing system 10 is removed, holes are used to attach a cutting guide to the distal femur F, and the cutting guide used to make subsequent bone cuts on the femur F. Once these bone cuts are made, a femoral prosthetic component is typically placed on the cut distal end of the femur. These final bone cuts thus determine the position and orientation of the femoral prosthetic component. Alternatively, positioning information may be used to orient/position bone cuts by some other means (not using a cutting guide), such by guiding a saw blade, rotary cutter, bur or the like to make the actual bone cuts. In some embodiments, position information may be used to guide a robotic surgical system, to enhance the procedure via a navigational system, or the like.

Also shown in FIG. 1E are two stationary femoral member attachment screws 22. These screws are used to removably attach stationary femoral member 18 to the distal femur F. Any other suitable attachment device(s) may be used instead of or in addition to attachment screws 22 to attach stationary femoral member 18 to the distal femur F For example, adhesives, pins and/or the like may be used in some embodiments.

FIGS. 2A-2C are anterior, posterior and side views, respectively, of an embodiment of femoral member 12. These figures show two screw holes 23 used for attaching stationary femoral member 18 to a distal femur. They also show drill guide apertures 24 which are formed by bushings 26 coupled with adjustable femoral member 17 and stationary femoral member 18. Bushings 26 move along slots 27 in stationary femoral member 17 as femoral member 12 is adjusted.

Figure 3A:
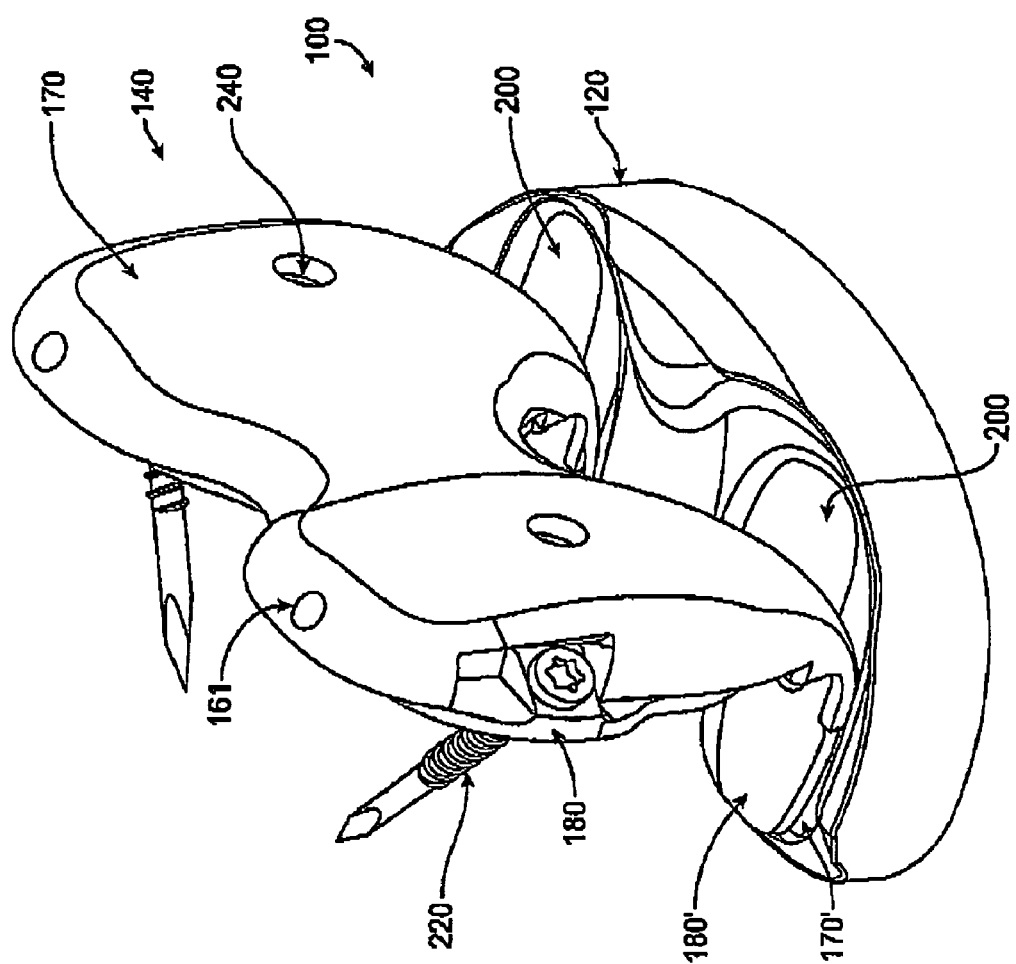
FIG. 3A is a front-perspective view of a knee balancing device according to one embodiment of the present invention.
Figure 3B:
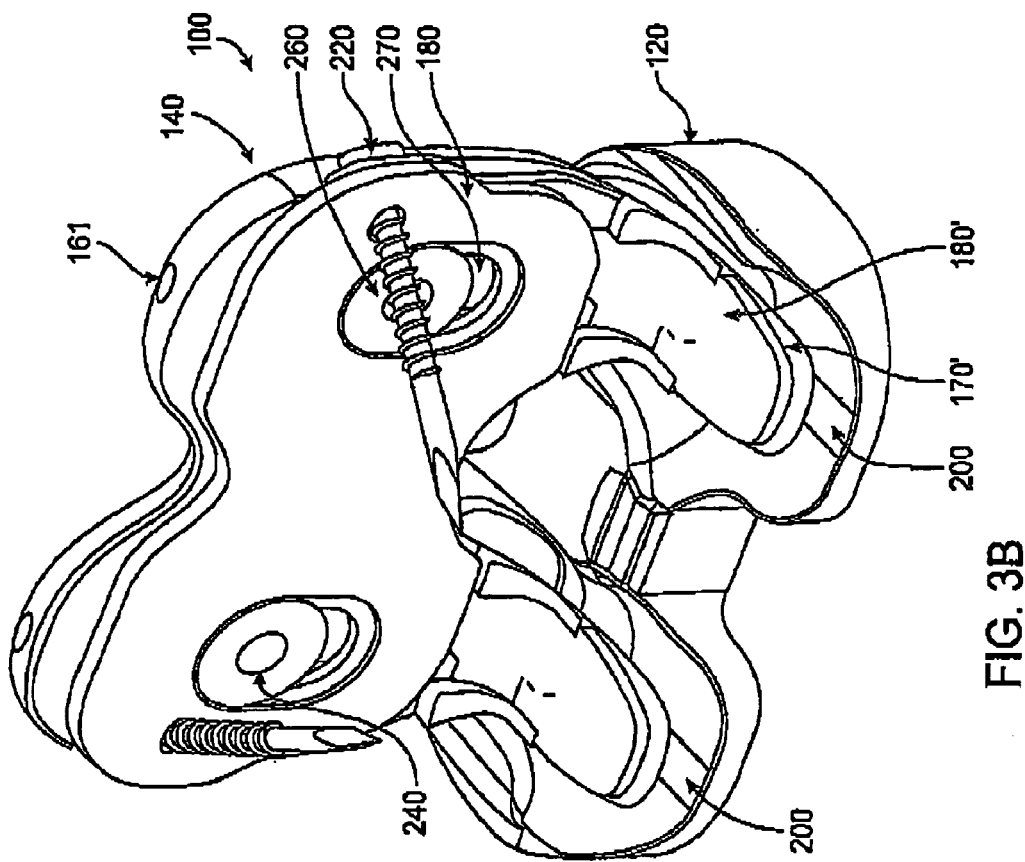
FIG. 3B is a rear-perspective view of the knee balancing device shown in FIG. 2A.

With reference now to FIGS. 3A and 3B, anterior and posterior perspective views, respectively, of an embodiment of a knee balancing system 100 are shown. Knee balancing system 100 suitably includes a femoral member 140 and a tibial member 120. Femoral member 140 may further include an adjustable femoral member 170 having adjustable posterior condylar members 170' and a stationary femoral member 180 having stationary posterior condylar members 180'. In some embodiments, adjustable femoral member 170 and adjustable posterior condylar member 170' will be one unitary piece or extrusion, while in other embodiments they may be two or more coupled pieces. Similarly, stationary femoral member 180 and stationary posterior condylar member 180' may comprise a one-piece construction or multiple pieces coupled together. In the embodiment shown, stationary femoral member 180 comprises a distal femoral plate coupled with two stationary posterior condylar members 180'. Any suitable configuration, combination or manufacturing process may be used in various embodiments.

Femoral member 140 may further include adjustment screw holes 161 for ingress/egress of adjustment screws (not shown), attachment screws 220, drill guide apertures 240, bushings 260, slots 270 and/or any other features described previously above. Tibial member 120 may suitably include two grooves 200 or depressions to provide for slidable coupling with femoral member 140. Generally, any of the features described above may be applied to knee balancing system 100.

Figure 3C:
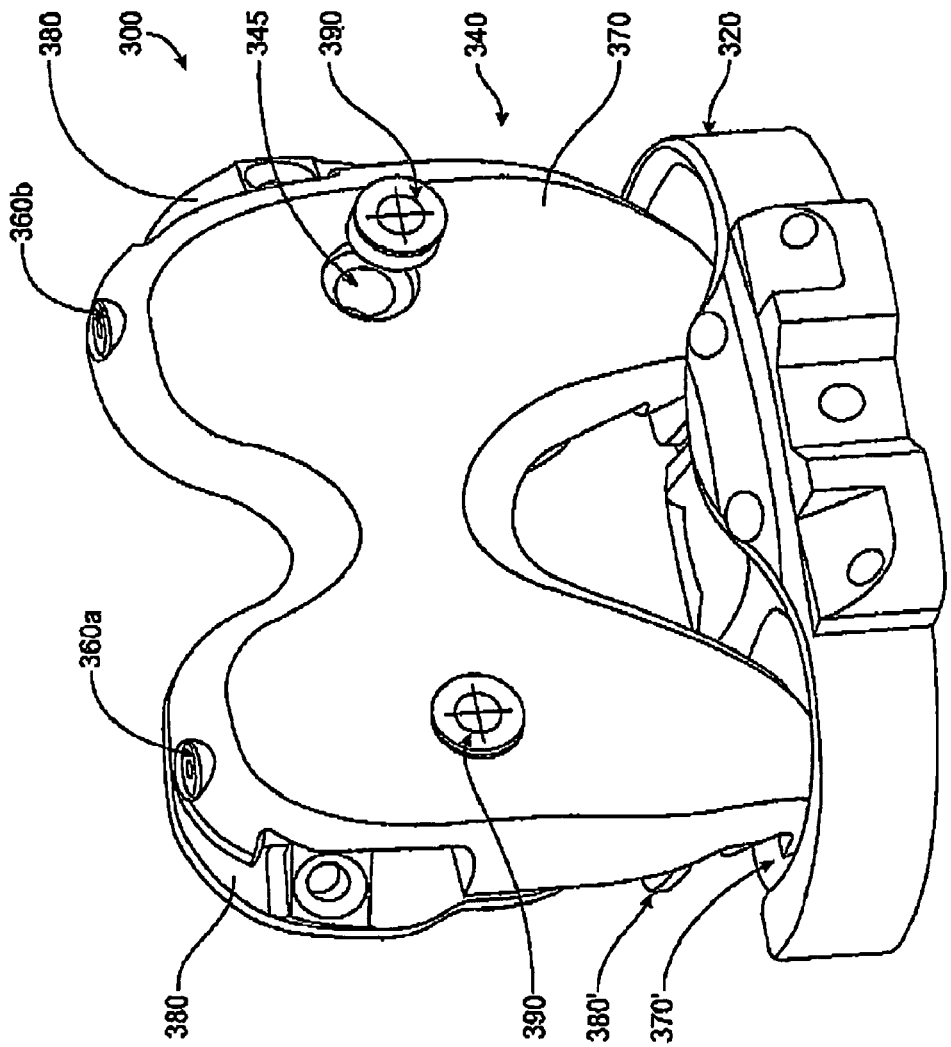
FIG. 3C is a front-perspective view a knee balancing device according to another embodiment of the present invention

Referring now to FIG. 3C, a knee balancing system 300 similar to that described above is shown in frontal-perspective view. System 300 includes a tibial member 320 and a femoral member 340, the femoral member 340 including an adjustable member 370 coupled with a stationary member 380. Adjustable member 370 includes two adjustable posterior condylar members 370', and stationary member 380 includes two stationary posterior condylar members 380'. In FIG. 3C, one adjustment member 360a has been adjusted to move adjustable posterior condylar portion 370' away from stationary posterior condylar member 380' on that side, which would increase the height of the joint space on that side if the device were in a knee joint, and would also rotate adjustable femoral member 370 slightly relative to the distal femur. The pictured embodiment includes two apertures 345 as positioning features, and disposed within apertures 345 are two fiducials 390 (or markers, sensors or the like) for providing positional information to a computer navigation system or robotic surgery system. Such positional information, for example, may include a dynamically balanced orientation of the knee to make subsequent bone cuts on the femur F.

Figure 4B:
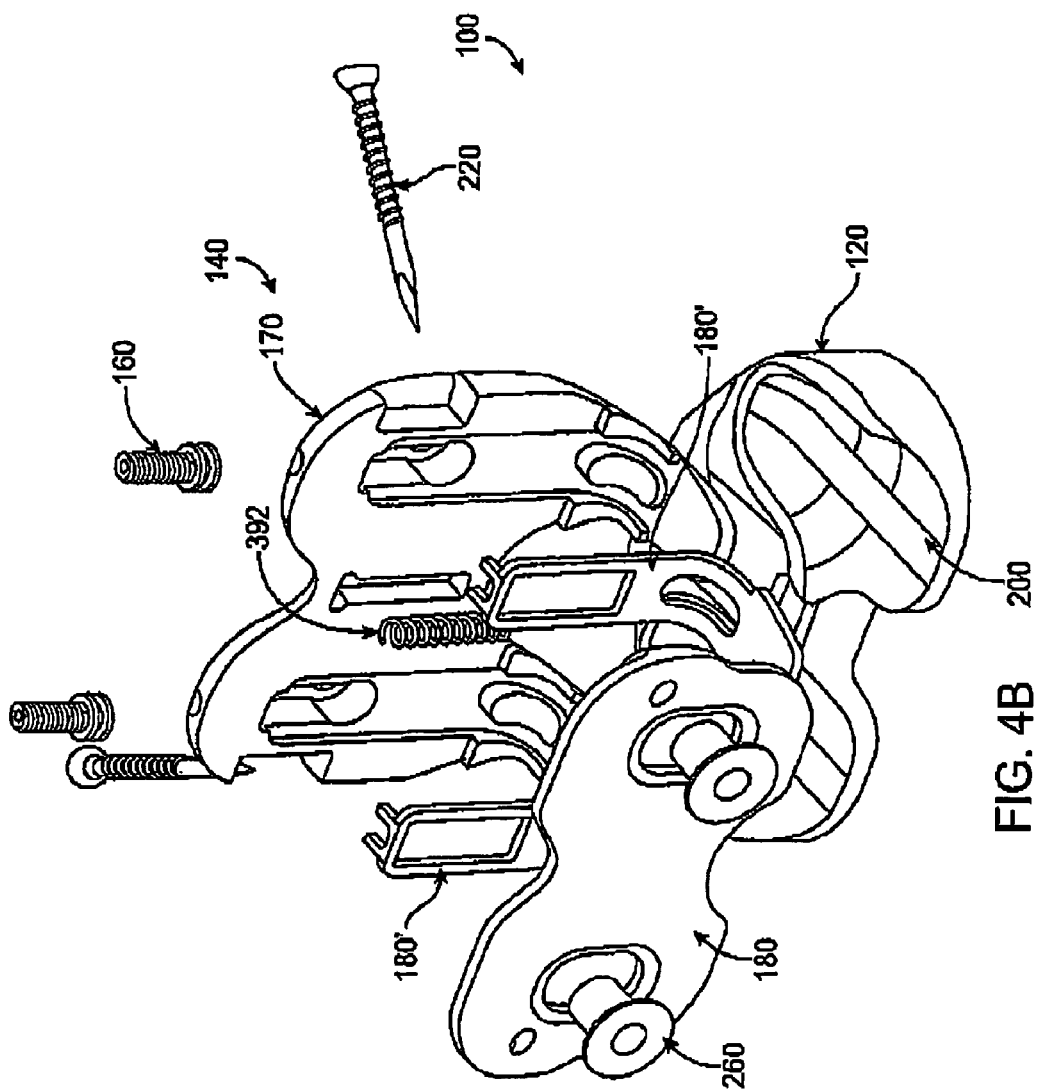
FIG. 4B is a rear-perspective, exploded view of the knee balancing device shown in FIG. 4A.

With reference now to FIGS. 4A and 4B, the embodiment of knee balancing system 100 from FIGS. 3A and 3B is shown in exploded view to more clearly show its component parts. In this embodiment, the component parts of knee balancing system 100 are the same as those shown and described above in reference to FIGS. 3A and 3B. It can be seen in FIGS. 4A and 4B that stationary femoral member 180 may comprise three coupled parts—a stationary femoral member distal plate 180 and two stationary posterior condylar members 180'. Such parts may be coupled by any suitable means, such as pressure fitting, sandwiching condylar members 180' between plate 180 and adjustable femoral member 170, screws, adhesives, and/or the like. Alternatively, stationary femoral member 180 may comprise one unitary piece or extrusion.

An additional part shown in FIG. 4B is a bias spring 300. Bias spring may be incorporated into femoral member 140 to allow for rotation of adjustable femoral member 170 relative to stationary femoral member 180. Alternative embodiments of knee balancing system 100 may include any other suitable mechanism for allowing such rotation, anterior-posterior adjustment, and/or any other suitable adjustment(s).

In an exemplary method for enhancing a TKA procedure, a femoral member is typically removably engaged with a distal femur of a knee. Usually, the distal femur will have been cut to form a surface for engaging the femoral member, but this is not required in all embodiments. A tibial member is also engaged with a proximal tibia of the knee, usually a cut horizontal surface of the tibia. This tibial member may be provided as part of a dynamic knee balancing system or may be an off-the-shelf tibial trial insert, in various embodiments. In different embodiments, the tibial member may be placed before the femoral member or vice versa. In one embodiment, the femoral and tibial members are engaged with the femur and tibia while the knee is in full or nearly full extension, though in alternative embodiments they may be placed in flexion. The height, thickness, or overall shape of the tibial member may often be selected to provide a desired amount and balance of ligament tension while the knee is in extension.

Generally, the knee is then moved from extension to flexion, and the femoral member is adjusted to adjust tension in the MCL, LCL, posterior cruciate ligament and/or other ligaments to achieve a desired ligament balance in flexion. The knee may then be moved through a range of motion, and one or more subsequent adjustments may be made to the femoral member to adjust and balance ligament tension through the range of motion. Most, if not all, such adjustments and movements may, in some embodiments, be possible while the patella of the knee remains in approximately its normal anatomical position over the knee. This is advantageous because patellar tracking, an important determinant of knee function, may be assessed and adjusted during the TKA procedure. Typically, the goal of the surgeon will be to achieve dynamic balancing of ligament tension through the range of motion of the knee. Once this balancing is achieved with the femoral and tibial members in place, the positioning feature(s) on the adjustable femoral member provide positional information to a surgeon, computer, robotic system and/or the like, to help facilitate completion of the TKA procedure. Using this positional information, subsequent cuts (or drilling, burring or other shaping methods) are applied to the femur, with such cuts/shaping determining how the femoral prosthetic component of the artificial knee joint will be positioned and oriented on the distal femur. The femoral prosthetic component is then placed accordingly.

It is contemplated that any of the devices, systems and methods described above may be incorporated with any suitable knee surgery procedures or systems currently used or discovered in the future. For example, inventive devices, systems and methods may be readily incorporated with any number of different visualization, navigation and/or robotic systems for performing a knee surgery, such as image-guided systems for performing, planning or enhancing a TKA procedure, robotic surgery systems such as the da Vinci® Surgical System provided by Intuitive Surgical, Inc. (Sunnyvale, Calif.), or the like. Any suitable imaging or visualization modality and technique may be used with various embodiments of the devices, systems and methods of the invention, such as but not limited to infrared or ultrasound imaging.

Many suitable modifications and additions to the devices described above may also be made without departing from the scope of the invention. For example, in some embodiments a measurement device may be included to measure ligament tension, and a display may additionally be included to display an amount of measured ligament tension to a user. In another embodiment, an amount of ligament tension may be "dialed in" or otherwise entered into the device such that the device will apply that amount of ligament tension within the knee.

Still other embodiments may include both tension measurement and tension dial-in capabilities.

Therefore, while the foregoing is a complete and accurate description of exemplary embodiments of the present invention, various embodiments of the devices, systems and methods described may include any number of modifications and additions. The exemplary descriptions above should thus not be interpreted to limit the scope of the invention as it is defined in the appended claims.

What is claimed is:

1. A device for enhancing a surgical procedure on a knee, the device comprising:
   a tibial member having a pair of complementary depressions, said tibial member being engageable with a surface of the proximal tibia;
   at least one stationary femoral member for removably attaching to a distal femur; and
   at least one adjustable femoral member having a first surface disposed to contact the tibial member when the knee is in extension and having a posterior condylar member including a medial femoral posterior condylar portion and a lateral femoral posterior condylar portion, said posterior condylar member being disposed at a substantially right angle relative to the first surface so that the medial and lateral femoral posterior condylar portions slidingly contact the complementary depressions in the tibial member when the knee is in flexion, said adjustable femoral member being movably engaged with the stationary femoral member to adjust tension in at least one ligament of the knee, the adjustable femoral member including an adjustment member that moves the adjustable femoral member in an anterior-posterior direction relative to the stationary femoral member for facilitating completion of the surgical procedure to enhance range of motion, stability or patella tracking of the knee; wherein the adjustable femoral member is movably engageable with said tibial member engaged with a proximal tibia to allow the knee to be moved through a range of motion from a fixed position to an extended position without removing the femoral and tibial members.

2. A device as in claim 1, wherein the at least one stationary femoral member is engageable with a surface at the distal end of the distal femur.

3. A device as in claim 1, wherein the adjustable femoral member is separately adjustable on a medial side and a lateral side of the femoral member to adjust tension in the at least one ligament.

4. A device as in claim 3, wherein adjusting on one side relative to the other side causes the adjustable femoral member to rotate relative to the distal femur.

5. A device as in claim 4, wherein the adjustment member comprises:
   at least one lateral adjustment member for adjusting a lateral portion of the adjustable member; and
   at least one medial adjustment member for adjusting a medial portion of the adjustable member.

6. A device as in claim 5, wherein the lateral and medial adjustment members are selected from the group consisting of screws, pins, levers, rods, springs, spring-loaded mechanisms and shape memory materials.

7. A device as in claim 1, wherein the at least one adjustable femoral member further has at least one distal femoral portion for emulating a distal surface of the femur.

8. A device as in claim 7, wherein the distal femoral portion, the, medial femoral posterior condylar portion, and the lateral femoral posterior condylar portion all comprise one piece or extrusion.

9. A device as in claim 7, wherein the at least one stationary femoral member comprises:
   at least one distal femoral plate for coupling the distal femoral portion of the adjustable femoral member to the distal femur; and
   wherein the posterior condylar member extends from the distal femoral portion to contact at least part of a medial posterior femoral condyle and a lateral posterior femoral condyle of the distal femur.

10. A device as in claim 9, wherein the distal femoral plate, the medial femoral posterior condylar member, and the lateral femoral posterior condylar member all comprise one piece or extrusion.

11. A device as in claim 9, wherein the medial femoral posterior condylar portion of the adjustable femoral member is adjustable relative to the medial femoral posterior condylar member of the stationary femoral member, and wherein the lateral femoral posterior condylar portion of the adjustable femoral member is separately adjustable relative to the lateral femoral posterior condylar member of the stationary femoral member.

12. A device as in claim 1, wherein the adjustable femoral member is adjustable relative to the stationary femoral member to separately adjust tension in at least one of a medial collateral ligament and a lateral collateral ligament of the knee.

13. A device as in claim 1, wherein the at least one adjustable femoral member comprises at least one self-adjusting member.

14. A device as in claim 13, wherein the at least one self-adjusting member comprises at least one of a spring-loaded member and a shape memory member.

15. A device as in claim 13, wherein the at least one self-adjusting member adjusts relative to the stationary femoral member to adjust tension in at least one of a medial collateral ligament and a lateral collateral ligament of the knee.

16. A device as in claim 1, wherein the at least one adjustable femoral member comprises a plurality of pre-adjusted femoral members, each having a different asymmetry relative to the stationary member; wherein one of the pre-adjusted members is selected for facilitating the surgical procedure to provide a desired range of motion when the surgical procedure is completed.

17. A device as in claim 1, wherein the adjustment member of the adjustable femoral member is selected from the group consisting of an aperture, a drill bit guide, a surface marker, a surface feature, a measurement device, an embedded marker, a fiducial, a transponder, a transceiver and a sensor.

18. A device as in claim 17, wherein the adjustment member facilitates at least one of placing a cutting guide on the distal femur for making bone cuts, making one or more bone cuts on the distal femur, and positioning a prosthetic femoral component on the distal femur.

19. A device as in claim 17, wherein the adjustment member comprises at least two apertures.

20. A device as in claim 19, wherein each of the at least two apertures is configured to guide a drill bit to form a hole in the distal femur for attaching a cutting guide to the femur.

21. A device as in claim 19, wherein each of the at least two apertures are configured to receive at least one of a marker, a fiducial, a transponder, a transceiver and a sensor.

22. A device as in claim 19, wherein the at least two apertures extend through the adjustable femoral member and through apertures in the stationary femoral member to provide access to the distal femur.

23. A device as in claim 22, wherein the at least two apertures are positioned slightly asymmetrically on the adjustable femoral member to provide for a built-in desired flexibility in the ligaments when the surgical procedure is completed.

24. A device as in claim 17, wherein at least one of the adjustable femoral member and the adjustment member is asymmetrically oriented relative to the stationary member to provide built-in enhanced range of motion when the surgical procedure is completed.

25. A device as in claim 24, further comprising multiple adjustable femoral members, each having a different asymmetry relative to the stationary member, wherein one of the multiple adjustable femoral members is selected for facilitating the surgical procedure to provide a desired range of motion when the surgical procedure is completed.

26. A device as in claim 1, wherein the tibial member comprises at least one shim, paddle, plate, bar, platform or rod.

27. A device as in claim 26, wherein the tibial member comprises a plurality of tibial shims having different thicknesses or heights, wherein any one of the plurality of shims may be selected for engaging with the surface of the proximal tibia to provide a desired amount of tension in the ligaments.

28. A device as in claim 27, wherein the tibial member further comprises a plate for removably attaching to the surface of the proximal tibia, disposed between the surface and the selected tibial shim.

29. A device, as in claim 1, wherein the femoral member and the tibial member are configured to be movably coupled via force provided by the at least one ligament of or adjacent the knee.

30. A device as in claim 1, wherein the femoral and tibial members, when engaged with the distal femur and proximal tibia respectively, are disposed primarily within a joint space between the distal femur and the proximal tibia.

31. A device as in claim 30, wherein a patella of the knee remains approximately in its anatomical position while the femoral and tibial members are engaged and the knee is moved through the range of motion.

32. A device as in claim 1, wherein the movable coupling of the femoral and tibial members allows for flexion and extension through the range of motion.

33. A device as in claim 32, wherein the range of motion comprises a range from approximately full extension of the knee to approximately full flexion of the knee.

34. A device as in claim 1, wherein the stationary femoral member comprises at least one material selected from the group consisting of plastics, composites, aluminum, stainless steel, composite, cobalt-chrome, titanium, and other metals.

35. A device as in claim 1, wherein the adjustable femoral member comprises at least one material selected from the group consisting of plastics, composites, aluminum, stainless steel, composite, cobalt-chrome, titanium, and other metals.

36. A device as in claim 1, further comprising at least one grasping member coupled with at least one of the stationary and adjustable femoral members for facilitating placement and/or removal of the device from the knee.

37. A device as in claim 1, wherein the adjustable femoral member is configured to be adjusted to identify at least one position on the distal femur for rotationally orienting a guiding device on the femur to make at least one bone cut for positioning of an implanted prosthetic femoral device, the position of the implanted device enhancing at least one of range of motion, stability and patella tracking of the knee.

38. A device as in claim 37, wherein the guiding devices is a cutting guide, a fiducial, a marker, a transponder or a transceiver and sensor.

39. A device as in claim 1, wherein the at least one stationary femoral member comprises:
   at least one distal femoral plate for removably attaching to the distal femur; and
   at least one stationary posterior condylar member extending substantially perpendicular from the distal femoral plate to contact at least part of a medial posterior femoral condyle or a lateral posterior femoral condyle of the distal femur.

40. A device as in claim 1, wherein the adjustable femoral member comprises a plate and the posterior condylar member extends substantially perpendicularly from the plate.

* * * * *